(12) United States Patent
Khemka et al.

(10) Patent No.: US 8,097,719 B2
(45) Date of Patent: Jan. 17, 2012

(54) MEROPENEM INTERMEDIATE IN NOVEL CRYSTALLINE FORM AND A METHOD OF MANUFACTURE OF MEROPENEM

(75) Inventors: Ashwin A. Khemka, Mumbai (IN); Pravin B. Shejul, Mumbai (IN); Amol V. Vyavahare, Mumbai (IN); Dhirendra Kumar Pandey, Mumbai (IN); Sachin N. Shete, Mumbai (IN); Hanumant K. Jadhav, Mumbai (IN); Nitn H. Kadam, Mumbai (IN)

(73) Assignee: Genesen Labs, Navi Mumbai (IN)

(*) Notice: Subject to any disclaimer, the term of this patent is extended or adjusted under 35 U.S.C. 154(b) by 509 days.

(21) Appl. No.: 12/255,668

(22) Filed: Oct. 22, 2008

(65) Prior Publication Data

US 2009/0299057 A1     Dec. 3, 2009

(30) Foreign Application Priority Data

Jul. 15, 2008   (IN) .................. 1483/MUM/2008

(51) Int. Cl.
C07D 477/20     (2006.01)
(52) U.S. Cl. ........................................ 540/350
(58) Field of Classification Search ............ 540/350
See application file for complete search history.

(56) References Cited

U.S. PATENT DOCUMENTS

| | | | | |
|---|---|---|---|---|
| 4,888,344 | A * | 12/1989 | Sunagawa et al. | 514/210.13 |
| 4,933,333 | A * | 6/1990 | Sunagawa et al. | 514/192 |
| 4,943,569 | A | 7/1990 | Sunagawa | |
| 5,122,604 | A | 6/1992 | Sunagawa et al. | |
| 5,424,422 | A * | 6/1995 | Sunagawa et al. | 540/200 |
| 5,700,930 | A * | 12/1997 | Feigelson et al. | 540/200 |
| 7,053,192 | B2 * | 5/2006 | Li et al. | 536/7.4 |
| 2005/0135999 | A1* | 6/2005 | Elomari et al. | 423/706 |
| 2007/0032435 | A1* | 2/2007 | Alani et al. | 514/18 |
| 2007/0197781 | A1* | 8/2007 | Tewari et al. | 540/350 |
| 2007/0249544 | A1* | 10/2007 | Himmelsbach et al. | 514/27 |
| 2007/0249827 | A1* | 10/2007 | Nadenik et al. | 540/350 |
| 2008/0004448 | A1* | 1/2008 | Wayne et al. | 546/276.7 |
| 2008/0089835 | A1* | 4/2008 | Burton | 423/706 |
| 2008/0103186 | A1* | 5/2008 | Glover et al. | 514/395 |
| 2008/0139569 | A1* | 6/2008 | Rocco et al. | 514/248 |
| 2008/0319024 | A1* | 12/2008 | Greil et al. | 514/342 |
| 2009/0069281 | A1* | 3/2009 | Austad et al. | 514/183 |
| 2009/0124652 | A1* | 5/2009 | Ach et al. | 514/293 |
| 2009/0137794 | A1* | 5/2009 | Mendez et al. | 540/78 |
| 2009/0176983 | A1* | 7/2009 | Dova et al. | 544/242 |
| 2009/0203705 | A1* | 8/2009 | Biagetti et al. | 514/252.02 |
| 2009/0239494 | A1* | 9/2009 | McKeown et al. | 514/494 |
| 2009/0264643 | A1* | 10/2009 | Surulichamy et al. | 540/350 |
| 2009/0299057 | A1* | 12/2009 | Khemka et al. | 540/350 |
| 2010/0004463 | A1* | 1/2010 | Manca et al. | 548/467 |
| 2010/0021539 | A1* | 1/2010 | Kowalski et al. | 424/464 |
| 2010/0240886 | A1* | 9/2010 | Nishino et al. | 540/350 |

FOREIGN PATENT DOCUMENTS

| | | | |
|---|---|---|---|
| EP | 1686129 A1 * | 8/2006 | |
| IN | 2007MU02068 | * | 2/2008 |
| WO | WO 9802439 A1 * | 1/1998 | |
| WO | 2005118586 A1 | 12/2005 | |
| WO | 2006035300 A3 | 4/2006 | |
| WO | WO 2006035300 A2 * | 4/2006 | |
| WO | 2007031858 A3 | 3/2007 | |

OTHER PUBLICATIONS

Sunagawa, Makoto et al, Journal of Antibiotics, 43(5), 519-32, 1990.*
Sunagawa, Makoto et al: "Synthetic studies of carbapenem and penem antibiotics. V. Efficient synthesis of the 1.beta.-methylcarbapenem skeleton" Chemical & Pharmaceutical Bulletin, 42(7), 1381-7 (1994).*
Matsumura H et al: Heterocycles, vol. 41, No. I, 1995, pp. 147-159.*
Tewari, IP.com Journal (2006), 6(8B), 4-5 (No. IPCOM000138815D), Aug. 4, 2006.*
Prashad, Tetrahedron Letters (1998), 39(39), 7035-7038.*
Nishioka, Journal of Labelled Compounds and Radiopharmaceuticals (1991), 29(9), 1051-60.*
Zhao, Chinese Journal of Medicinal Chemistry, vol. 15, No. 2, Apr. 2005, SUM 64, pp. 97-99.*
Translation of Zhao, Chinese Journal of Medicinal Chemistry, vol. 15, No. 2, Apr. 2005, SUM 64, pp. 97-99.*

* cited by examiner

Primary Examiner — Mark Berch

(57) ABSTRACT

The present invention relates to novel crystalline form of (4-Nitrobenzyl (4R,5S,6S)-(3-{(3S,5S)-5-[(dimethylamino) carbonyl]-1-[(4-nitrophenoxy)carbonxyl]pyrrolidin-3-yl}thio-6-[(1R)-1-hydorxyehtyl]-4-methyl-7-oxo-1-azabi-cyclo[3.2.0].hept-2-ene-2-carboxylate) of compound Formula I as well as an improved process for the preparation of meropenem trihydrate of compound Formula II

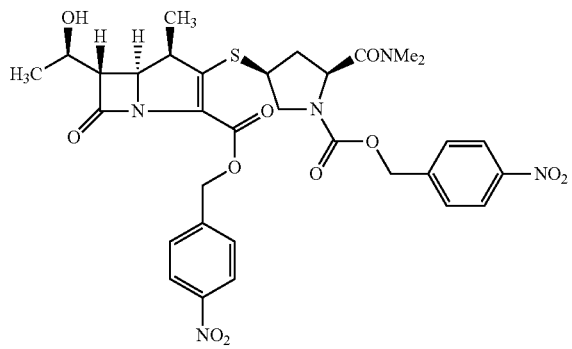

Formula I

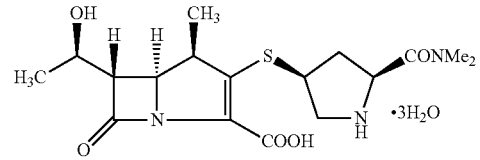

Formula II wherein, PNB represent P-nitro benzyl group and PNZ represent P-nitrobenzyloxycarbonyl group.

3 Claims, 1 Drawing Sheet

MEROPENEM INTERMEDIATE IN NOVEL CRYSTALLINE FORM AND A METHOD OF MANUFACTURE OF MEROPENEM

FIELD OF INVENTION

The present invention relates to novel crystalline form of (4-Nitrobenzyl (4R,5S,6S)-(3-{(3S,5S)-5-[(dimethylamino)carbonyl]-1-[(4nitrophenoxy)carbonxyl]pyrrolidin-3-yl}thio-6-[(1R)-1-hydorxyethyl]-4-methyl-7-oxo-1-azabicyclo[3.2.0].hept-2-ene-2-carboxylate) of Formula I below, also herein after referred as protected meropenem, is a key intermediate of meropenem.

Formula-I

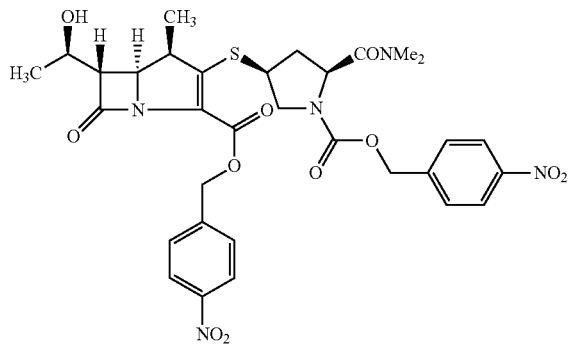

Wherein, PNB represent P-nitro benzyl group and PNZ represent P-nitrobenzyloxycarbonyl group.

Furthermore, the present invention relates to an improved and industrially applicable process for production of meropenem trihydrate, chemically designated as trihydrate salt of ((4R,5S,6S)-3-[[(3S,5S)-5-(Dimethylcarbamoyl)-3-pyrrolidinyl]thio]-6-[(1R)-1-hydroxy-ethyl]-4-methyl-7-oxo-1-azabicyclo[3.2.0]hept-2-ene-2-carboxylic acid)) of Formula II below.

Formula II

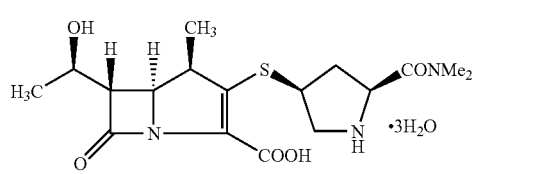

BACKGROUND OF INVENTION

Meropenem, an ultra-broad spectrum injectable antibiotic used to treat a wide variety of infections, including meningitis and pneumonia, was first disclosed in U.S. Pat. No. 4,888,344. It is a beta-lactam antibiotic and belongs to the subgroup of carbapenem, similar to imipenem and ertapenem.

U.S. Pat. No. 4,888,344 provides a process for the preparation of the crystalline trihydrate of meropenem. U.S. Pat. Nos. 4,943,569 and 5,122,604 provide similar processes for the preparation of meropenem trihydrate. (4-Nitrobenzyl(4R, 5S,6S)-(3-{(3S,5S)-5-[(dimethylamino)carbonyl]-1-[(4-nitrophenoxy)carbonxyl]pyrrolidin-3-yl}thio-6-[(1R)-1-hydorxyethyl]-4-methyl-7-oxo-1-azabicyclo[3.2.0].hept-2-ene-2-carboxylate) known as key intermediate of meropenem (Formula I) chemically known ((4R,5S,6S)-3-[[(3S,5S)-5-(Dimethylcarbamoyl)-3-pyrrolidinyl]thio]-6-[(1R)-1-hydroxy-ethyl]-4-methyl-7-oxo-1-azabicyclo[3.2.0]hept-2-ene-2-carboxylic acid)), Formula II which is synthetic broad spectrum, carbapenem antibiotic.

The compound of Formula I in non crystalline form e.g amorphous form, in form of oil, foamy solid generally is known with poor materials properties such as stability or purity and isolating properties compared to crystalline forms. In synthesis, the obtainment of product in crystalline form is necessary as the same is available with more purity. Moreover, the crystalline materials have substantially better stability than amorphous form.

WO2006/035300 A2 describes a process for preparing Meropenem by using biphasic solvent system for the deprotection of compound of Formula (V), which is similar to the teachings provided in U.S. Pat. No. 4,943,569, where ethyl acetate was added after the hydrogenation to remove organic impurity.

Formula-V

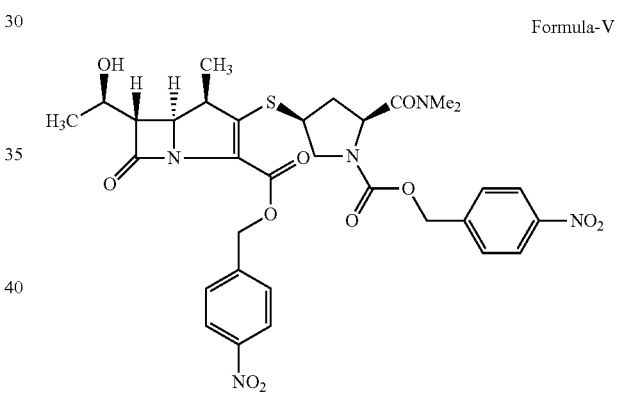

WO2006/035300A2 further claims a process for preparing Meropenem trihydrate in which the penultimate compound of Formula-V shown above was not isolated. This teaching is similar to the disclosure of U.S. Pat. No. 4,888,344, where, the suggestion has given to the extent that a Meropen trihydrate can be directly crystallized out from the resultant aqueous concentrate.

WO2005/118586 A1 claims crystalline penultimate compound of Formula I and a process for preparing this intermediate. According to this publication, the intermediate is crystallized out either from concentrating the mother liquor in alkyl alkanoate such as ethyl acetate or by the addition of anti-solvent such as cyclohexane or heptane to the mother liquor in ethyl acetate. Since this publication describes the use of multiple solvent systems, the processes are not commercially viable from industrial point of view owing to multiple solvent recoveries, thus, adding further cost to the production.

As per U.S. Pat. No. 4,888,344 in example 1, Meropenem is dissolved in water, where upon small amount of meropenem crystals formed and further addition of acetone yielded meropenem trihydrate. Since the sterile preparation requires complete dissolution for sterile filtration, this technique is not found attractive.

According to the above mentioned patent literature, Meropenem trihydrate was obtained by subjecting the aqueous reaction mass after the deprotection of protecting group to hydrogenation at high pressure, and also to reverse osmosis (if necessary), followed by adding water-miscible organic solvent such as ethanol, iso-propanol, acetone, tetrahydrofuran (THF), dioxane, acetonitrile, etc.

In our embodiment, such a type of explosive step like hydrogenation at high pressure has been avoided to obtain meropenem trihydrate.

Therefore, there is need to provide a cost effective and eco-friendly process for preparation of meropenem trihydrate. Accordingly the present invention provides a process which devoid of the use of expensive and hazardous reagents and critical reaction parameters. Also, the solvent used as reaction medium is recovered to greater extent after the completion of reaction, which makes the process commercially applicable for industrial scale furthermore, the embodiment is deprotection reaction carried out at 6.5 to 6.9 pH of reaction mass by using the carbonate water or phosphate buffer or morpholine buffer of pH-7 so as to achieve maximum yield and good purity.

OBJECT OF INVENTION

In one embodiment, the main object of the present invention is to provide the novel crystalline form of protected meropenem. Another objective of the present invention is to provide commercially applicable process with suitable reaction parameters as well as less no of operations for preparation of meropenem trihydrate. Another objective of the invention is to provide cost effectiveness and environment friendly process of preparation over the existing prior art.

SUMMARY OF INVENTION

The present invention is mainly directed to a novel crystalline form of protected meropenem which has a good stability over amorphous form and furthermore, to provide a cost effective and eco friendly process for the preparation of meropenem trihydrate.

In a preferred aspect, compound of Formula A, (4-nitrobenzyl(4R,5R,6S)-3-[(diphenoxyphosphoryl)oxy]-6-[(1R)-1-hydroxyethyl]-4-methyl-7-oxo-1-azabicyclo[3.2.0]hept-2-ene-2-carboxylate) and compound B, (4-nitrobenzyl(2S',4S)-2-[(dimethylamino)carbonyl]-4-mercaptopyrrolidine-1-carboxylate) are condensed in a mixture of acetonitrile and dimethyl acetamide at −5 to −10° C., followed by the addition of di-isopropylethylamine in dropwise manner at the same temperature. After completion of the reaction, the reaction mass is extracted with ethyl acetate and distilled out completely with a concomitant stoichiometric addition of methyl ethyl ketone and acetone with a continued stirring at 0-5° C., followed by the addition of water and small amounts of seeding to produce a novel crystalline form of protected meropenem.

The process for the same is depicted in scheme I as follows:

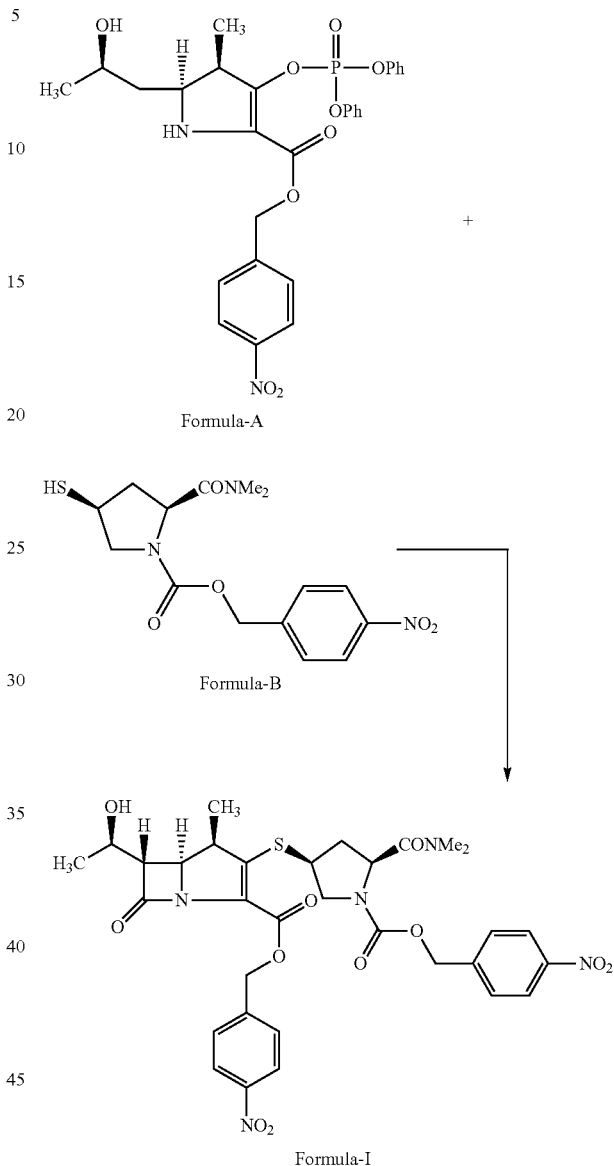

In another aspect, the deprotection of protected meropenem is achieved by hydrogenation at atmospheric pressure in mixture of tetrahydrofuron and water as solvent media with palladium on charcoal at room temperature at pH of reaction mass 6.5 to 7.5 to get meropenem trihydrate in desirable yield and purity.

The process for the same is depicted as follows;

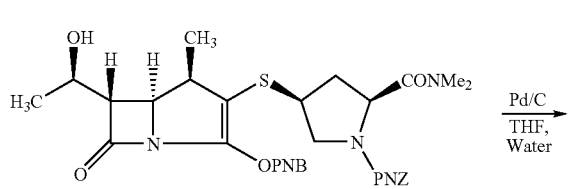

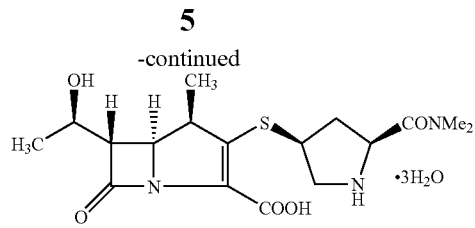

Wherein, PNB represents P-nitro a benzyl group and PNZ represents a P-nitrobenzyloxycarbonyl group.

Thus according to the present invention, the compound of Formula I is obtained in novel crystalline form which has been found under the exemplified conditions. The novel crystalline form (Figure-I) of meropenem intermediate, which has above mentioned advantages, can be used in preparation of meropenem.

The certain crystalline form found under the certain condition has been elaborately described in forgoing examples. The physiochemical properties of the compound Formula-I in novel crystalline form may be described as follows.

a) External appearance:
  Light yellow, needle type crystals.
b) Melting point
  151-153° C.
c) X-ray powder diffractogram The compound of Formula-I in crystalline form shows characteristic bands at the 2-theta diffraction angles at about 5.01, 7.0, 10.3, 15.5, 17.0, 20.8, 22.6 and 26.4.

X-ray powder difractogram of the compound Formula I in crystalline form recorded on AXS-Bruker-D-8 advance, equipped with Brag-Brentano θ-θ gonion meter using a tube voltage of 40 Kv and tube current 40 mA with a step size 0.013°, and, time of steps of 1 second over an angular range of 3-45°, 2 theta. The sample was exposed to the Cu K alpha radiations (lambda=1.5418 A°) and evaluation was carried out using software EVA.

Powder diffractogram of (4-Nitrobenzyl(4R,5S,6S)-(3-{(3S,5S)-5-[(dimethylamino)carbonyl]-1-[(4-nitrophenoxy)carbonxyl]pyrrolidin-3-yl}thio-6-[(1R)-1-hydorxyethyl]-4-methyl-7-oxo-1-azabicyclo[3.2.0].hept-2-ene-2-carboxylate), are provided below in table 1.

TABLE 1

| Caption | Angle 2-Theta° | d value Angstrom | Intensity Count | Intensity % |
|---|---|---|---|---|
| A = 5.099° | 5.099 | 17.31756 | 1946 | 100 |
| A = 7.028° | 7.028 | 12.56692 | 205 | 10.5 |
| A = 10.336° | 10.336 | 8.55159 | 722 | 37.1 |
| A = 12.515° | 12.515 | 7.0674 | 143 | 7.4 |
| A = 12.824° | 12.824 | 6.89778 | 196 | 10.1 |
| A = 13.120° | 13.12 | 6.74238 | 233 | 12 |
| A = 13.460° | 13.46 | 6.57325 | 266 | 13.7 |
| A = 13.935° | 13.935 | 6.35002 | 287 | 14.7 |
| A = 14.148° | 14.148 | 6.25482 | 313 | 16.1 |
| A = 15.472° | 15.472 | 5.72235 | 832 | 42.7 |
| A = 15.751° | 15.751 | 5.62166 | 463 | 23.8 |
| A = 16.987° | 16.987 | 5.21529 | 1407 | 72.3 |
| A = 17.561° | 17.561 | 5.0462 | 615 | 31.6 |
| A = 18.335° | 18.335 | 4.83496 | 482 | 24.8 |
| A = 19.085° | 19.085 | 4.64653 | 230 | 11.8 |
| A = 19.719° | 19.719 | 4.49848 | 519 | 26.7 |
| A = 20.101° | 20.101 | 4.41393 | 445 | 22.8 |
| A = 20.769° | 20.769 | 4.27349 | 777 | 39.9 |
| A = 22.112° | 22.112 | 4.0168 | 226 | 11.6 |
| A = 22.541° | 22.541 | 3.94135 | 595 | 30.6 |
| A = 23.300° | 23.3 | 3.81463 | 622 | 32 |
| A = 24.031° | 24.031 | 3.70026 | 458 | 23.5 |
| A = 24.885° | 24.885 | 3.5751 | 188 | 9.7 |
| A = 25.345° | 25.345 | 3.51129 | 282 | 14.5 |

TABLE 1-continued

| Caption | Angle 2-Theta° | d value Angstrom | Intensity Count | Intensity % |
|---|---|---|---|---|
| A = 26.421° | 26.421 | 3.37066 | 363 | 18.7 |
| A = 27.525° | 27.525 | 3.23795 | 236 | 12.1 |
| A = 28.925° | 28.925 | 3.08437 | 217 | 11.1 |
| A = 31.233° | 31.233 | 2.8615 | 130 | 6.7 |

The compound of Formula I may be obtained by condensing (4-nitrobenzyl (4R,5R,6S)-3-[(diphenoxyphosphoryl)oxy]-6-[(1R)-1-hydroxyethyl]-4-methyl-7-oxo-1-azabicyclo[3.2.0]hept-2-ene-2-carboxylate) and (4-nitrobenzyl(2S', 4S)-2-[(dimethylamino)carbonyl]-4-mercaptopyrrolidine-1-carboxylate) in acetonitrile and dimethyl acetamide as solvent media furthermore added diisopropyl ethylamine. After completion of the reaction, the compound was distilled out the complete solvent media and added to a combination of ketone based solvents for crystallization, and finally, added to a polar protic solvent to complete crystallization.

The ketone based solvents are ethyl methyl ketone, methyl butyl ketone, acetone, isobutyl ketone, diethyl ketone etc. or mixture thereof, but preferably acetone and methyl ethyl ketone are used to obtain crystalline form of compound of Formula I.

Polar protic solvents are selected from water, methanol, dimethyl sulphoxide, dimethyl acetate, but preferably water is used to get complete crystallization. The compound Formula I is crystallized and isolated in the usual manner having excellent stability and having typical purity more than 99.0% by HPLC area percentages.

Another aspect of the present invention is to provide industrially applicable process for preparation of meropenem of Formula II from crystalline compound Formula I by hydrogenation at atmospheric pressure, whereby protected meropenem i.e. the compound of Formula I, is deprotected by using palladium on carbon in a solvent mixture of tetrahydrofuran and an aqueous solution of sodium carbonate or phosphate buffer or morpholine buffer of pH-7 at a temperature of 30-35° C. and the pH of reaction mass should be 6.5 to 6.9 so as to exert a desired yield and purity, which has been exemplified in the foregoing description as well as in examples. Preferably, Formula I is deprotected at a temperature between and including 30° C. and 32° C.

DETAIL DESCRIPTION OF INVENTION

Figure 1:
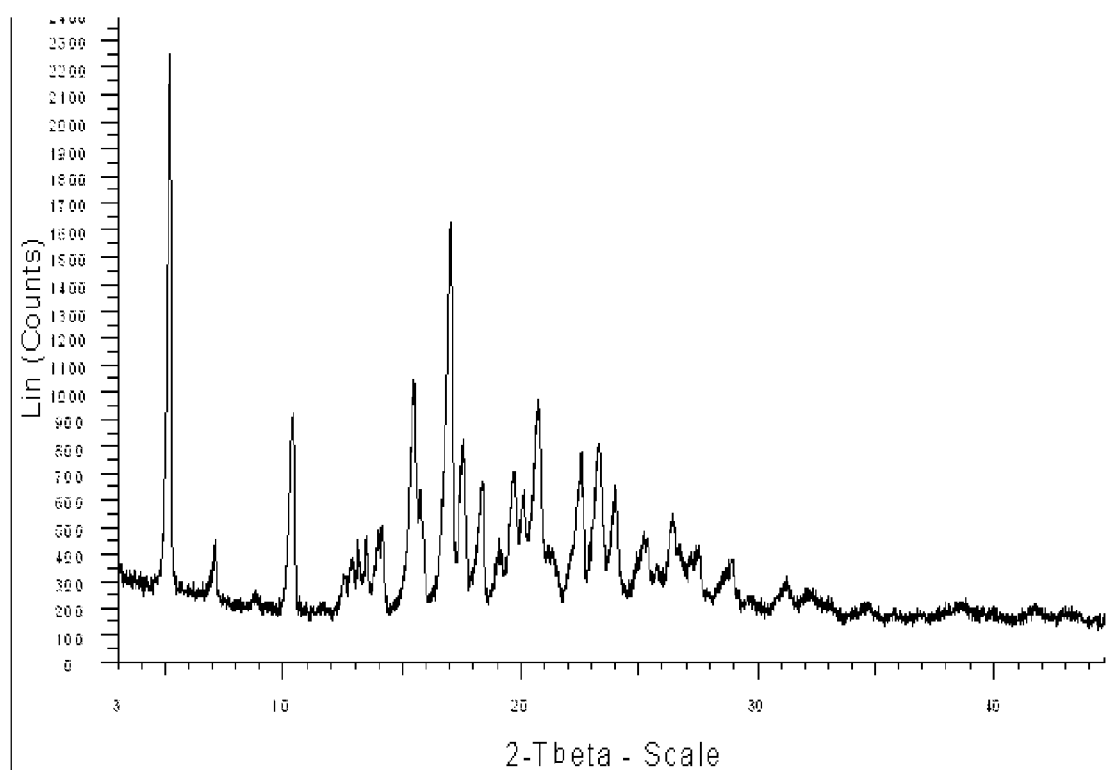
FIG. 1 depicts an X-ray powder difractogram of the novel crystalline form of meropenem intermediate

While the invention will now be described in detail in connection with certain preferred and optional embodiments, so that various aspects thereof may be more fully understood and appreciated, it is not intended to limit the invention to these particular embodiments.

The method described herein below provides substantial benefits relative to previously used or suggested production methods. For example, the starting materials, intermediates, liquid media, and catalysts used are relatively easier to handle and to dispose of, if necessary. Importantly, the present method provides high yields of the desired product or products so that substantial process efficiencies are achieved.

Preparation of novel crystalline polymorph of protected meropenem preperation is depicted as follows:

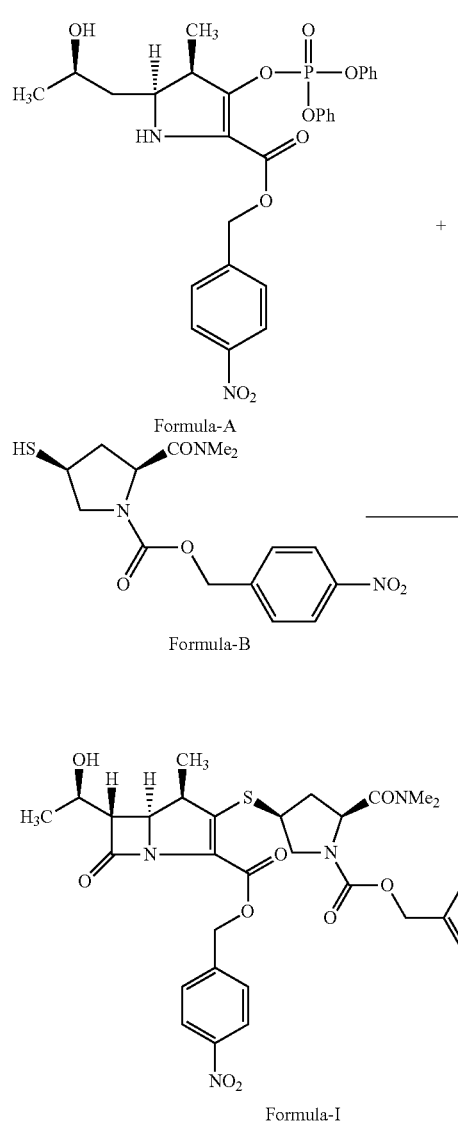

Formula-A

Formula-B

Formula-I

In a preferred embodiment, Formula A is condensed with Formula B in solvent media acetonitrile in presence of polar protic solvent dimethyl acetamide and added diisopropyl ethylamine as reaction accelerator at a temperature ranging from −10 to −5° C. up to completion of reaction. The reaction is monitored by HPLC (High performance liquid chromatography) followed by extraction with ethyl acetate. Furthermore, complete distillation of ethyl acetate added stoichiometric proportion of methyl ethyl ketone and acetone to the said reaction mass and continued with stirring at 0-5° C. for 14 hours. Finally added cold water and small amount of seeding and allow to stir at same temperature for complete crystallization.

Thus, according to preferred embodiment, molar ratio of Formula A and Formula B is in stoichiometric proportion. Acetonitrile as solvent media is used 2-4 times, preferably, 4 times w.r.t Formula A and polar protic solvents are DMSO, dimethyl acetamide, dimethyl formamide etc. but preferably dimethyl acetamide used in at least 1-2 times w.r.t to Formula A, followed by addition of diisopropyl ethylamine in proportion of 2-4 times with respect to Formula B, preferably 2 times in such a way that to maintain reaction temperature to accelerate fastly. Finally, after completion of the reaction, the reaction mass is extracted by ethyl acetate and distilled out completely followed by addition of methyl ethyl ketone and acetone to set crystallization point in stoichiometric proportion, preferably 1:1.25 and for complete crystallization polar miscible solvent like water is added at least in one proportion with respect to mixture of ethyl methyl ketone and acetone.

The process described as above is used to manufacture proteceted meropenem in crystalline form with desirable yield in about 90-95% and with a purity above 99%. Furthermore, protected meropenem is treated with palladium on charcoal (Pd/C) in a mixture of tetrahydrofuran and carbonate water or phosphate buffer or morpholine buffer of pH-7 so as to retain reaction mass pH 6.5 to 6.9 at temperature of 30-35° C. for 2-3 hours to achieve a maximum yield. After completion of the reaction, the reaction mass is degasified and charcoalised to form a clear aqueous layer which is further reduced by distillation and finally acetone is added at a maintained temperature of 0-5° C. for 3 hours to get crystalline meropenem trihydrate in pure form.

Thus, in another embodiment, the invention provides isolation of meropenem trihydrate from reaction mass which comprises the following steps:
  a) After completion of the reaction, adjusting the pH of reaction mass in range 6-7 by using sodium carbonate solution if necessary;
  b) Degasifying the reaction mass followed by charcoalizing and filtering at ambient temperature;
  c) Reducing the aqueous layer under vacuum below 35° C.;
  d) Adding acetone to the above aqueous layer at temperature of 0-5° C. and continuing the stirring for 3 hours for complete precipitation;
  e) Filtering and washing the cake by acetone to get pure meropenem trihydrate.

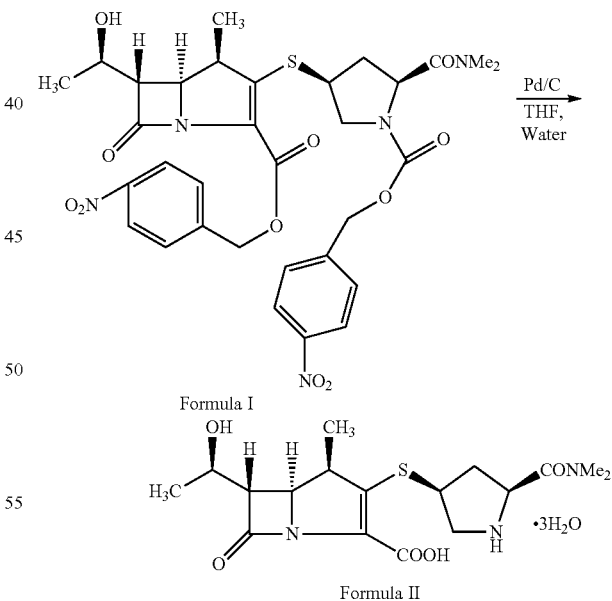

Formula I

Formula II

Wherein, PNB represent P-nitro benzyl group and PNZ represent P-nitrobenzyloxycarbonyl group.

The deprotection step as depicted above is carried out at a temperature of 30-35° C. in monophasic solvent system with a mole ratio of protected meropenem and palladium on charcoal as 1:0.25. The pH of the reaction mass plays a vital role in acceleration of the reaction to achieve good yield. The pH of the reaction mass should be in range 6-7 so as to get a maximum yield and the side product p-nitro toluene will be in the non-aqueous layer and the maximum meropenem will go into the aqueous layer by maintaining water of pH 7, so as to achieve a maximum yield.

The process of the present invention to manufacture meropenem trihydrate has been well depicted in forgoing Examples.

The following examples are offered to provide the general state of preparation for meropenem trihydrate so that the person with ordinary skill in the art has a sufficiently clear and complete explanation of this invention, but should not be considered as a limitation to the essential aspect of the object thereof, as is explained below.

EXAMPLE 1

Preparation of Protected Meropenem 4-nitrobenzyl (4R,5R,6S)-3-[(diphenoxyphosphoryl) oxy]-6-[(1R)-1-hydroxyethyl]-4-methyl-7-oxo-1-azabicyclo[3.2.0]hept-2-ene-2-carboxylate (10 gm) Formula-A and 4-nitrobenzyl (2S,4S)-2-[(dimethylamino)carbonyl]-4-mercaptopyrrolidine-1-carboxylate (6.122 gm) Formula-B was dissolved in 60 ml acetonitrile and 3 ml dimethyl acetamide at ambient temperature. The solution was stirred under same condition for 10 minutes to get clear solution and cool to a temperature of minus −10° C. Di-isopropylethyl amine (9.15 ml) was added dropwise under stirring conditions to the above solution at −10° C. and continued the reaction for 90 minutes at the same reaction parameters. After completion of the reaction, 150 ml ethyl acetate was added in said reaction mass, the ethyl acetate layer was extracted by acidic water till to get pH 6-7 of the extracted acidic water, then dried over sodium sulphate and distilled off up to free solid. Next a 1:1 mixture of 50 ml methyl ethyl ketone and acetone was added and allowed to keep for 14 hours for crystallization at 0-5° C., finally 30 ml cold water with a small amount of seeding was added for complete crystallization. The solid was filtered and washed with 10 ml mixture of diethyl ether and ethyl acetate to obtain pure 4-Nitrobenzyl (4R,5S,6S)-3-({(3S,5S)-5-[(dimethylamino)carbonyl]-1-[(4-nitrophenoxy)carbonxyl]pyrrolidin-3-yl}thio)-6-[(1R)-1-hydorxyethyl]-4-methyl-7-oxo-1-azabicyclo[3.2.0].hept-2-ene-2-carboxylate (referred as protected meropenem)

Yield=10.20 gm. purity=99% above.

EXAMPLE II

Preparation of Meropenem Trihydrate

Charged 4-Nitrobenzyl(4R,5S,6S)-3-({(3S,5S)-5-[(dimethylamino)carbonyl]-1-[(4-nitrophenoxy)carbonxyl]pyrrolidin-3-yl}thio)-6-[(1R)-1-hydroxyethyl]-4-methyl-7-oxo-1-azabicyclo[3.2.0].hept-2ene-2-carboxylate (referred as protected meropenem) obtained from Example-I in 50 ml of tetra hydrofuran and 2.5 gms 10% palladium on an activated charcoal and added 50 ml of aqueous solution of sodium bi carbonate or phosphate buffer or morpholine buffer to maintain the pH at about 6.5-6.9 The above reaction mixture was hydrogenated at atmospheric pressure for 3 hours at 30-35° C. After completion of reaction, the mixture was filtered and degasified completely. The aqueous layer was charcoalised for 30 minutes to get a clear transparent layer, followed by washing the aqueous layer with 20 ml ethyl acetate. The aqueous layer is concentrated under vacuum below 35° C. and 400 ml acetone was added to the aqueous layer slowly at temperature about 0-5° C. The resultant mass was stirred for 3 hours at the same temperature. The separated solid was filtered, washed with chilled acetone and dried at ambient temperature to get meropenem trihydrate.

Yield=5.10 gm.

EXAMPLE III

Preparation of Sterile Meropenem Trihydrate

Charged 4-Nitrobenzyl(4R,5S,6S)-3-({(3S,5S)-5-[(dimethylamino)carbonyl]-1-[(4-nitrophenoxy)carbonxyl]pyrrolidin-3-yl}thio)-6-[(1R)-1-hydroxyethyl]-4-methyl-7-oxo-1-azabicyclo[3.2.0].hept-2-ene-2-carboxylate (referred as protected meropenem) obtained from Example-I in 50 ml of tetra hydrofuran and 2.5 gms of 10% palladium on activated charcoal and added 50 ml of aqueous solution of sodium bi carbonate or phosphate buffer or marpholine buffer of pH-7 to maintained pH 6.5-6.9. The above reaction mixture was hydrogenated at atmospheric pressure for 2 hours at 30-35° C. After completion of reaction, the mixture was filtered and degasified completely. The aqueous layer was charcoalised for 30 minutes to get clear transparent layer, which was washed with 20 ml ethyl acetate. The combined aqueous layers were filtered through a series of 0.45 and 0.22µ under aseptic condition and the filtrate was concentrated under vacuum below 35° C. 400 ml acetone previously filtered through 0.22µ was added to the aqueous layer under aseptic condition slowly at controlled temperature about 0-5° C. and the resultant mass was stirred for 3 hours at the same temperature. The separated solid was filtered, washed with chilled acetone and dried at ambient temperature to get meropenem trihydrate

We claim:

1. A method for preparation of meropenem trihydrate having the structure

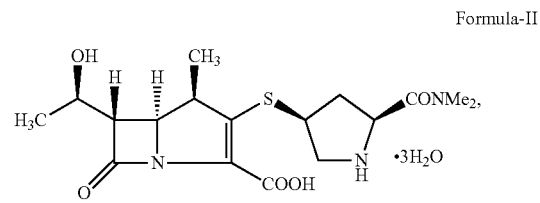

Formula-II from a protected meropenem of the structure

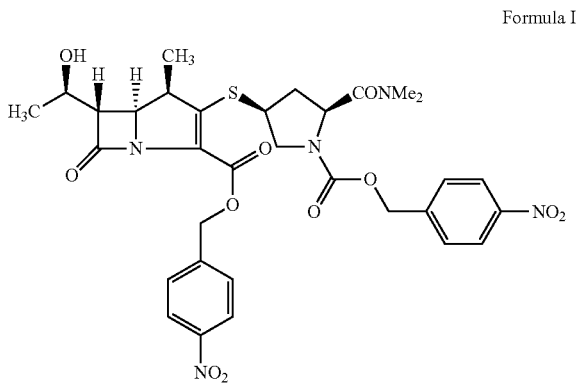

Formula I comprising the steps of:
  deprotecting the protected meropenem of Formula I by hydrogenation at an atmospheric pressure at a temperature between and including 30° C. and 35° C. in at least one water miscible solvent selected from the group consisting of acetone, methanol, tetrahydrofuran, ethanol or a mixture thereof, at a pH 6.5 to 6.9;
  in the deprotection reaction the pH of reaction mass is in 6.5 to 6.9 maintained by using an aqueous solution of sodium carbonate or a phosphate buffer or a morpholine buffer of pH of 7;
  degasifying and charcoalizing the reaction mass followed by adding acetone at a temperature between and including 0° C. and 5° C. in order to obtain meropenem trihydrate.

2. The method for preparation of meropenem trihydrate of claim 1, using an aqueous solution of sodium carbonate or phosphate buffer or morpholine buffer having a pH of 7 and wherein the solvent is tetrahydrofuran.

3. The method for preparation of meropenem trihydrate of claim 1, wherein the deprotection is carried out at a temperature between and including 30° C. and 32° C.

\* \* \* \* \*